(12) United States Patent
Adam

(10) Patent No.: US 10,926,278 B2
(45) Date of Patent: Feb. 23, 2021

(54) FLUID PRODUCT DISPENSING DEVICE

(71) Applicant: APTAR FRANCE SAS, Le Neubourg (FR)

(72) Inventor: Fabien Adam, Aviron (FR)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

(21) Appl. No.: 16/628,100

(22) PCT Filed: Jul. 3, 2018

(86) PCT No.: PCT/FR2018/051647
§ 371 (c)(1),
(2) Date: Jan. 2, 2020

(87) PCT Pub. No.: WO2019/008264
PCT Pub. Date: Jan. 10, 2019

(65) Prior Publication Data
US 2020/0122173 A1    Apr. 23, 2020

(30) Foreign Application Priority Data
Jul. 6, 2017 (FR) ...................................... 1756400

(51) Int. Cl.
*B05B 11/02* (2006.01)
*A61M 11/00* (2006.01)
(Continued)

(52) U.S. Cl.
CPC ......... *B05B 11/025* (2013.01); *A61M 5/2466* (2013.01); *A61M 5/30* (2013.01);
(Continued)

(58) Field of Classification Search
CPC ............. B05B 11/0008; B05B 11/3074; B05B 11/025; A61M 11/007; A61M 15/0041; A61M 5/2466; A61M 5/30; A61M 15/08
See application file for complete search history.

(56) References Cited

U.S. PATENT DOCUMENTS 5,427,280 A * 6/1995 Fuchs ............... A61M 15/0065
                                                           222/320
5,469,989 A * 11/1995 Graf .................. A61M 15/0025
                                                           222/82
(Continued)

FOREIGN PATENT DOCUMENTS

FR    2 847 834 A1    6/2004

OTHER PUBLICATIONS

International Preliminary Report on Patentability with a Translation of Written Opinion in International Application No. PCT/FR2018/051647, dated Jan. 16, 2020.
(Continued)

*Primary Examiner* — Jeremy Carroll
(74) *Attorney, Agent, or Firm* — Sughrue Mion, PLLC

(57) ABSTRACT

A fluid dispenser device having a body (1) with a dispenser orifice (2) and a perforator element (4), the body containing a reservoir (10) with at least two doses of fluid and having a proximal axial opening closed by a membrane (30) and a distal axial opening closed by a piston (20) to dispense one dose of fluid on each actuation. The reservoir is axially movable relative to the body between a rest position in which said perforator element does not pass through the membrane and a dispensing position in which the perforator element passes through the membrane. A perforator spring (6) is provided to urge the reservoir towards the rest position, and the membrane is adapted to close after each actuation, when said perforator element withdraws from the reservoir.

13 Claims, 3 Drawing Sheets

(51) Int. Cl.
  *A61M 5/24* (2006.01)
  *B05B 11/00* (2006.01)
  *B05C 17/005* (2006.01)
  *A61M 15/00* (2006.01)
  *A61M 5/30* (2006.01)
  *A61M 15/08* (2006.01)

(52) U.S. Cl.
  CPC ...... *A61M 11/007* (2014.02); *A61M 15/0041* (2014.02); *A61M 15/08* (2013.01); *B05B 11/0008* (2013.01); *B05B 11/3074* (2013.01); *B05C 17/00586* (2013.01); *B05C 17/00593* (2013.01); *A61M 2005/247* (2013.01)

(56) References Cited

U.S. PATENT DOCUMENTS

| | | | |
|---|---|---|---|
| 6,382,465 B1* | 5/2002 | Greiner-Perth | A61M 15/0065 222/309 |
| 6,446,839 B1* | 9/2002 | Ritsche | A61M 5/3158 222/153.13 |
| 2002/0117513 A1* | 8/2002 | Helmlinger | B05B 11/025 222/82 |
| 2005/0029288 A1 | 2/2005 | Heldt et al. | |
| 2007/0000950 A1 | 1/2007 | Ingram et al. | |
| 2008/0210229 A1 | 9/2008 | Corbacho | |
| 2017/0259285 A1* | 9/2017 | Petit | B05B 11/02 |

OTHER PUBLICATIONS

International Search Report of PCT/FR2018/051647 dated Oct. 8, 2018 [PCT/ISA/210].

\* cited by examiner

FLUID PRODUCT DISPENSING DEVICE

CROSS REFERENCE TO RELATED APPLICATIONS

This application is a National Stage of International Application No. PCT/FR2018/051647, filed Jul. 3, 2018, claiming priority to French Patent Application No. 1756400, filed Jul. 6, 2017.

The present invention relates to a fluid dispenser device, in particular in the form of a nasal spray.

Fluid dispenser devices are well known in the state of the art.

Generally, such devices comprise a reservoir containing several doses of fluid to be dispensed, and on which there is mounted a dispenser member, such as a metering pump, for dispensing a dose on each actuation. A drawback of metering pumps relates to priming, which requires one or more prior actuations before guaranteeing that a complete dose is dispensed. This problem exists not only before the first actuation, but it may also exist before each actuation, especially when, between two successive actuations, there is a lapse of time, typically several days. Unfortunately, with certain fluids, such as dangerous or particularly expensive pharmaceuticals, typically for anti-migraine treatments, such priming actuations are not desirable, since they necessarily dispense a small amount of fluid, leading to risks of poor metering for the user and/or of wasting an active agent that is expensive. For example, for an anti-migraine treatment requiring four doses of medication to be dispensed in succession, it is necessary to fill the reservoir with practically five or six doses of fluid in order to guarantee that four doses are dispensed completely. The increased cost of active agent is thus very high.

Devices also exist comprising a reservoir containing fluid to be dispensed, and a piston that is slidably mounted in said reservoir, and that is moved for selectively dispensing the fluid contained in said reservoir. When the reservoir contains a plurality of doses of fluid to be dispensed during a plurality of successive actuations, the piston is moved in a plurality of successive actuation strokes, such that a first dose is dispensed during a first actuation, a second dose is dispensed during a second actuation, etc. With that type of multi-dose device, there exists a problem of the fluid that remains in the reservoir after the first use being spoilt. Specifically, during the first actuation, the reservoir is opened, such that its content can become contaminated, in particular when the device is stored between two successive actuations. Unfortunately, depending on the type of fluid that is dispensed by the device, in particular when it is a medication, it may be important to avoid any risk of contamination.

Documents FR 2 847 834, US 2005/029288, US 2007/000950, and US 2008/210229 describe prior-art devices.

An object of the present invention is to provide a fluid dispenser device that does not have the above-mentioned drawbacks.

An object of the present invention is thus to provide a fluid dispenser device that avoids any fluid being wasted before and/or after each actuation.

Another object of the present invention is to provide a fluid dispenser device that ensures the fluid is protected between two actuations.

Another object of the present invention is to provide such a fluid dispenser device that is simple and inexpensive to manufacture and to assemble.

The present invention thus provides a fluid dispenser device comprising: a body that is provided with a dispenser orifice and with a perforator element, said body containing a reservoir that contains at least two doses of fluid, said reservoir including a proximal axial opening that is closed by a membrane, and a distal axial opening that is closed by a piston that is slidably mounted in said reservoir so as to dispense one dose of fluid on each actuation, said reservoir being axially movable relative to said body between a rest position in which said perforator element does not pass through said membrane, and a dispensing position in which said perforator element passes through said membrane, a perforator spring being provided between said body and said reservoir, so as to urge said reservoir towards its rest position, said membrane being adapted to close in leaktight manner after each actuation, when said perforator element withdraws from said reservoir.

Advantageously, said membrane is formed as a structure comprising at least two layers made out of different materials.

Advantageously, said membrane includes an inner layer that is made out of butyl rubber and that is in contact with the fluid.

Advantageously, said inner layer has thickness lying in the range about 0.6 millimeters (mm) to about 0.7 mm.

Advantageously, said membrane includes an outer layer that is made out of polyisoprene.

Advantageously, said outer layer has thickness lying in the range about 1 mm to about 1.5 mm.

Advantageously, said membrane is made by calendering and cross-linking, and then by cutting out, in particular by punching.

Advantageously, said piston co-operates with a piston rod that extends axially out from said reservoir, said piston rod co-operating, at its end remote from said piston, with an actuator member.

Advantageously, said actuator member is axially movable in said body between a rest position and an actuated position, the actuator member including at least one deformable tab that co-operates with teeth of said piston rod, so as to perform successive actuations.

Advantageously, a return spring is mounted between the actuator member and the body, so as to return said actuator member into its rest position after each actuation.

Advantageously, said perforator element is secured to an insert that is fastened in said body, upstream from said dispenser orifice.

Advantageously, a spray profile is provided directly upstream from said dispenser orifice.

These advantages and characteristics of the present invention, and others, appear more clearly from the following detailed description, given by way of non-limiting examples, and with reference to the accompanying drawings, and in which.

The present invention is described below with reference to one very diagrammatic embodiment. The shapes and dimensions of the various component parts are only illustrative and not limiting. Naturally, the present invention applies more generally to any type of device containing at least two doses.

Figure 5:
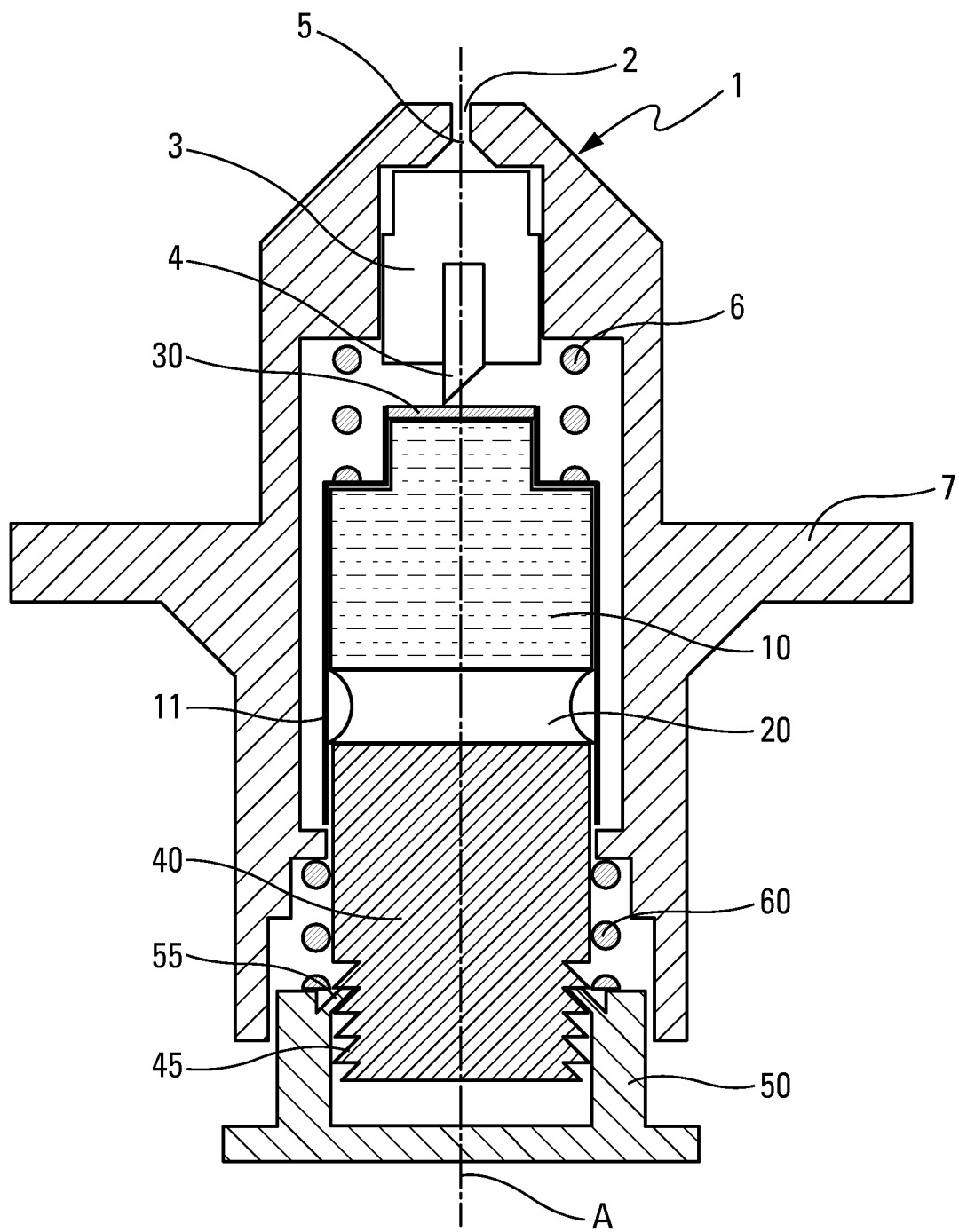
FIG. 5 is a view similar to the view in FIG. 4, after actuation, with the device ready for the next actuation.

The terms "proximal" and "distal" are relative to the dispenser orifice. The term "axial" refers to the longitudinal central axis A shown in FIG. 5.

With reference to the figures, the dispenser device comprises a body 1 that is provided with a dispenser orifice 2.

Said body 1 contains a reservoir 10 that contains a plurality of doses of fluid, in particular a liquid medication, e.g. for spraying into a user's nose. The reservoir 10 advantageously includes a hollow body 11 that is substantially cylindrical, including a proximal axial opening and a distal axial opening. The distal opening is closed in leaktight manner by a piston 20 that is slidably mounted in said reservoir 10. The proximal opening is closed by a membrane 30. The drawings show a proximal opening formed on a cylindrical portion of smaller diameter, but this is not essential, and the hollow body 11 forming the reservoir 10 may also be completely cylindrical.

Said piston 20 co-operates with a piston rod 40 that extends axially out from said reservoir 10. Said piston rod 40 thus co-operates at its proximal axial end with said piston 20, and it co-operates at its distal axial end with an actuator member 50.

Upstream from said dispenser orifice 2, the body 1 includes an insert 3 that is mounted in stationary manner in said body 1, said insert 3 supporting a hollow perforator element 4, such as a needle or a cannula, for perforating said membrane 30 of the reservoir 10.

Figure 3:
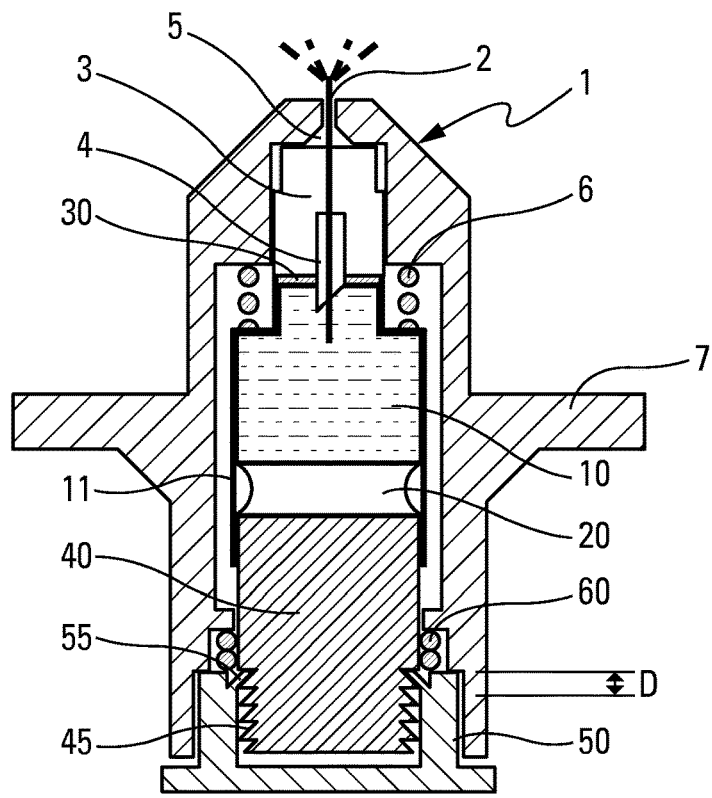
FIG. 3 is a view similar to the view in FIG. 2, during actuation, while the first dose is being dispensed.

Said insert 3 may also define a spray profile 5 directly upstream from said dispenser orifice 2, so as to generate a spray, in particular a nasal spray. The spray profile 5 may be formed in conventional manner in the proximal axial edge of said insert 3 and/or in the end wall of said body 1, that surrounds said dispenser orifice 2 and that faces said proximal axial edge of the insert 3. The spray profile 5 may include swirl channels and a swirl chamber. In very diagrammatic manner and by means of a vertical line, FIG. 3 shows a dose being dispensed, but naturally in the presence of a spray profile, the fluid would pass laterally between the body 1 and the insert 3, in conventional manner.

The body 1 includes a finger-rest element 7 that is advantageously formed integrally with said body 1, but that, in a variant, could be assembled around said body 1.

The reservoir 10 is mounted to slide axially in said body 1 between a rest position in which said perforator element 4 does not pass through said membrane 30, and a dispensing position in which said perforator element 4 passes through said membrane 30. A perforator spring 6 is provided between said body 1 and said reservoir 10, so as to urge said reservoir 10 towards its rest position.

In order to perform successive actuations of the device, said actuator member 50 is axially movable inside said body 1 between a rest position and an actuated position. As can be seen in the figures, the actuator member 50 includes at least one deformable tab 55 that is adapted to co-operate with teeth 45 of the piston rod 40, so as perform successive actuations.

A return spring 60 is mounted between the actuator member 50 and the body 1, so as to return said actuator member 50 into its rest position after each actuation.

Operation of the device shown in the figures is as follows.

Figure 1:
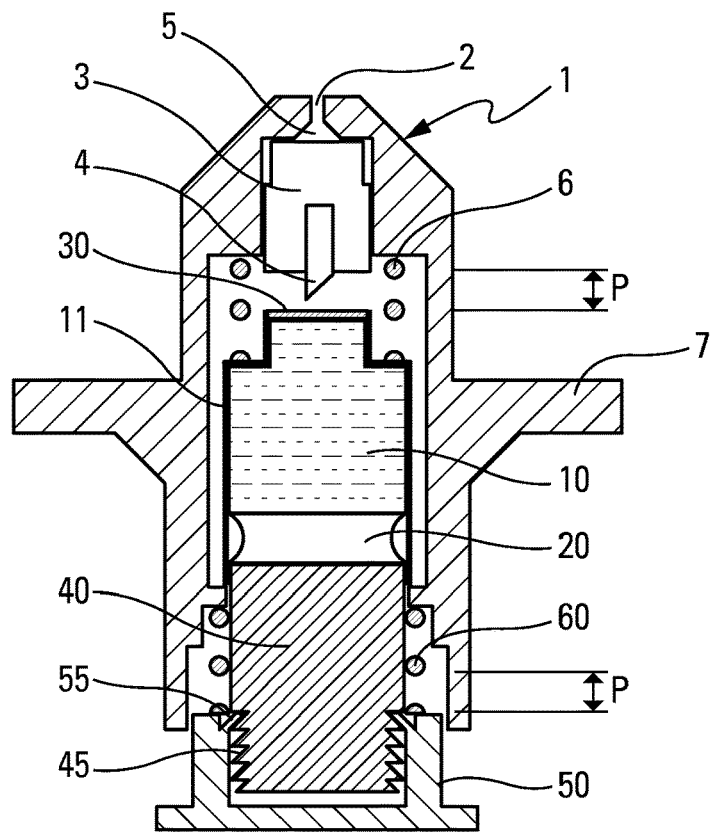
FIG. 1 is a diagrammatic section view of a fluid dispenser device in an advantageous embodiment of the present invention, before first use.
Figure 2:
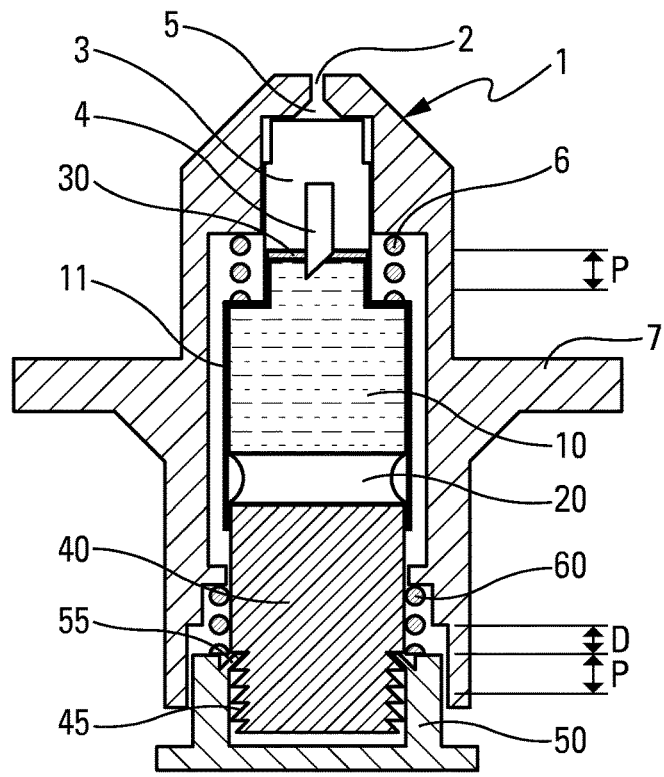
FIG. 2 is a view similar to the view in FIG. 1, during actuation, after the reservoir has been perforated, and before the first dose has been dispensed.

In the rest position in FIG. 1, the reservoir 10 is isolated from the atmosphere firstly by the piston 20 and secondly by the membrane 30. When the user presses simultaneously on the finger rest 7 and on the actuator member 50, said actuator member 50 moves inside the body 1. Since the force required to move the piston 20 in the reservoir 10 is greater than the force required to compress the perforator spring 6 and the return spring 60, axial movement of the actuator member 50 thus moves the reservoir 10 and the piston rod 40 axially towards the dispenser orifice 2, as can be seen in FIG. 2, with the perforator element 4 penetrating into the reservoir 10 by passing through the membrane 30. This compresses the perforator spring 6, and also the return spring 60 in part. FIGS. 1 and 2 show the perforating stroke P, which is identical for the actuator member 50 and for the reservoir 10. In the FIG. 2 position, the reservoir 10 co-operates with the insert 3, which forms an abutment to the axial movement of the reservoir 10. Advantageously, during this perforating stroke, the actuator member 50 co-operates with the body 1, e.g. by friction, in order to accumulate energy in the user's fingers.

Continuing the axial movement of the actuator member 50 towards the dispenser orifice 2 thus causes the piston 20 to move inside the reservoir 10, and thus causes a dose of fluid to be dispensed. The fluid is thus pushed by said piston 20 through the perforator element 4 towards the spray profile 5, then out from the device through the dispenser orifice 2. Advantageously, the energy accumulated in the user's fingers during the perforating stroke makes it possible to generate sufficient force to move the piston 20 in the reservoir 10, thereby guaranteeing that the complete dose is dispensed.

After a dose of fluid has been dispensed, the device is in the position shown in FIG. 3. Advantageously, the actuator member 50 is in abutment against a portion of the body 1, thereby making it possible to define, with accuracy, the metering stroke D shown in FIGS. 2 and 3.

Figure 4:
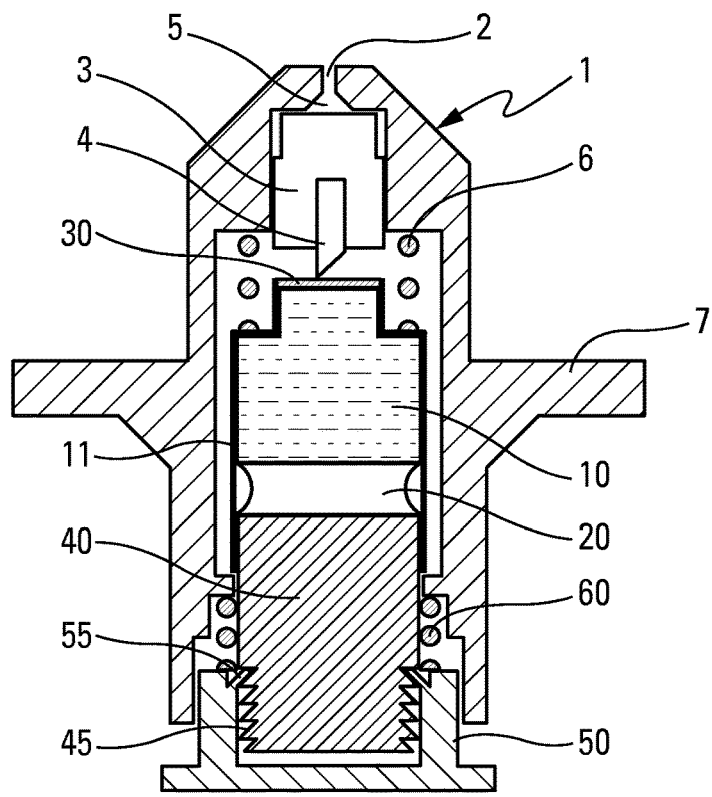
FIG. 4 is a view similar to the view in FIG. 3, during actuation, after the first dose has been dispensed, and after the reservoir has been closed.

When the user relaxes pressure on the actuator member 50, the perforator spring 6 initially returns the reservoir 10 towards its rest position. The perforator element 4 withdraws from the reservoir 10, and the membrane 30 closes, so that the content of the reservoir is isolated from the atmosphere once again. FIG. 4 shows this position.

The return spring 60 then returns the actuator member 50 towards its rest position. While the actuator member 50 is returning towards its rest position under the effect of the return spring 60, the tabs 55 deform and come to snap-fasten below the next tooth 45 of the piston rod 40, thereby enabling the user to actuate the device once again in order to dispense the next dose of fluid.

In the invention, the membrane 30 is adapted to close in leaktight manner after each actuation, when the perforator element 4 withdraws from the reservoir 10.

Advantageously, the membrane 30 is formed as a structure having two layers, with two different materials:

an inner layer made out of butyl rubber that is in contact with the fluid, that is inert relative to the fluid, and that typically has thickness lying in the range about 0.6 mm to about 0.7 mm; and an outer layer that is made out of polyisoprene for its automatic closing property, and that typically has thickness lying in the range about 1 mm to about 1.5 mm.

Advantageously, the membrane is made by calendering and cross-linking, and then by cutting out, in particular by punching. In a first variant, the two raw materials are calendered and cross-linked together. In a second variant, a first material is calendered and cross-linked, then the second material is calendered on the first material, then cross-linked.

Other materials having similar properties may be envisaged. In addition, a single-layer structure, preferably made out of butyl rubber, could be envisaged if the number of doses to be dispensed is small, typically lying in the range 2 doses to 5 doses. In addition, a membrane having more than two layers would also be possible.

The present invention thus provides a fluid dispenser device that presents in particular the following advantages:
priming is not necessary since there is no metering chamber to fill, as in a metering pump; the first actuation of the device thus delivers a dose that is complete;
no loss of fluid associated with priming actuations;
the dimensions of the reservoir are adapted to the number of doses to be dispensed and to the metering stroke of the piston;
the dose volume can easily be adjusted via the dimensions of the reservoir and/or the metering stroke; and
the fluid contained in the reservoir is isolated from the atmosphere between two actuations, thereby limiting the risks of bacterial or bacteriological contamination.

The present invention is described above with reference to an advantageous embodiment that is not limiting, and any useful modification can be applied to the present invention without going beyond its ambit, as defined by the accompanying claims.

The invention claimed is:

1. A fluid dispenser device comprising: a body that is provided with a dispenser orifice and with a perforator element, said body containing a reservoir that contains at least two doses of fluid, said reservoir including a proximal axial opening that is closed by a membrane, and a distal axial opening that is closed by a piston that is slidably mounted in said reservoir so as to dispense one dose of fluid on each actuation, wherein said reservoir is axially movable relative to said body between a rest position in which said perforator element does not pass through said membrane, and a dispensing position in which said perforator element passes through said membrane, a perforator spring being provided between said body and said reservoir, so as to urge said reservoir towards its rest position, said membrane being adapted to close in leaktight manner after each actuation, when said perforator element withdraws from said reservoir.

2. A device according to claim 1, wherein said membrane is formed as a structure comprising at least two layers made out of different materials.

3. A device according to claim 2, wherein said membrane includes an inner layer that is made out of butyl rubber and that is in contact with the fluid.

4. A device according to claim 3, wherein said inner layer has thickness lying in the range about 0.6 mm to about 0.7 mm.

5. A device according to claim 2, wherein said membrane includes an outer layer that is made out of polyisoprene.

6. A device according to claim 5, wherein said outer layer has thickness lying in the range about 1 mm to about 1.5 mm.

7. A device according to claim 2, wherein said membrane is made by calendering and cross-linking, and then by cutting out.

8. The device according to claim 7, wherein said cutting out is performed by a punching operation.

9. A device according to claim 1, wherein said piston co-operates with a piston rod that extends axially out from said reservoir, said piston rod co-operating, at its end remote from said piston, with an actuator member.

10. A device according to claim 9, wherein said actuator member is axially movable in said body between a rest position and an actuated position, the actuator member including at least one deformable tab that co-operates with teeth of said piston rod, so as to perform successive actuations.

11. A device according to claim 9, wherein a return spring is mounted between the actuator member and the body, so as to return said actuator member into its rest position after each actuation.

12. A device according to claim 1, wherein said perforator element is secured to an insert that is fastened in said body, upstream from said dispenser orifice.

13. A device according to claim 1, wherein a spray profile is provided directly upstream from said dispenser orifice.

* * * * *